(12) United States Patent
Hamilton (10) Patent No.: US 11,712,527 B1
(45) Date of Patent: Aug. 1, 2023

(54) KIT FOR LOCATING A VEIN

(71) Applicant: Tanya Hamilton, Greensboro, NC (US)

(72) Inventor: Tanya Hamilton, Greensboro, NC (US)

( * ) Notice: Subject to any disclaimer, the term of this patent is extended or adjusted under 35 U.S.C. 154(b) by 531 days.

(21) Appl. No.: 16/847,805

(22) Filed: Apr. 14, 2020

(51) Int. Cl.
| | |
|---|---|
| *A61M 5/42* | (2006.01) |
| *A61F 13/00* | (2006.01) |
| *A61L 15/20* | (2006.01) |
| *A61L 15/24* | (2006.01) |
| *A61K 31/167* | (2006.01) |
| *A61L 15/44* | (2006.01) |

(52) U.S. Cl.
CPC ....... *A61M 5/427* (2013.01); *A61F 13/00063* (2013.01); *A61K 31/167* (2013.01); *A61L 15/20* (2013.01); *A61L 15/24* (2013.01); *A61L 15/44* (2013.01); *A61M 5/422* (2013.01); *A61L 2300/204* (2013.01); *A61L 2300/402* (2013.01); *A61M 2205/0238* (2013.01); *A61M 2205/364* (2013.01)

(58) Field of Classification Search
CPC ............... A61M 5/427; A61M 5/422; A61M 2205/0238; A61M 2205/364; A61F 13/00063; A61K 31/167; A61L 15/20; A61L 15/24; A61L 15/44; A61L 2300/204; A61L 2300/402
See application file for complete search history.

(56) References Cited

U.S. PATENT DOCUMENTS

| | | |
|---|---|---|
| 6,274,167 B1 | 8/2001 | Margiotta |
| D477,086 S | 7/2003 | Tsuruda |
| 7,883,487 B2 | 2/2011 | Shantha |
| 9,186,469 B2 | 11/2015 | Murphy |
| 9,302,085 B2 | 4/2016 | Boyle |
| 10,272,211 B1 | 4/2019 | Cooke |
| 2002/0006435 A1 | 1/2002 | Samuels |
| 2015/0133844 A1* | 5/2015 | Montulet ............ A61F 13/0259 602/44 |
| 2020/0069595 A1* | 3/2020 | Neshat ................ A61K 9/0063 |

FOREIGN PATENT DOCUMENTS

WO      2010005680      1/2010

\* cited by examiner

*Primary Examiner* — Robert A Wax
*Assistant Examiner* — Quanglong N Truong
(74) *Attorney, Agent, or Firm* — Kyle A. Fletcher, Esq.

(57) ABSTRACT

The kit for locating a vein is configured for use in inserting an intravenous (IV) catheter into a targeted vein of a patient. The kit for locating a vein is a transparent structure. The kit for locating a vein: a) removably attaches to the skin of the patient; b) numbs the skin of the patient; c) generates a vasomotor response; d) provides the ability to insert the IV catheter into the targeted vein while the kit for locating a vein remains attached to the patient; and, e) forms a dressing that captures bodily fluids. The kit for locating a vein comprises a parchment sheeting, a working media, a transparent pocket, and a plurality of apertures. The parchment sheeting, the working media, and the transparent pocket form a transparent composite textile structure. The plurality of apertures are apertures that are formed through the composite textile structure.

18 Claims, 6 Drawing Sheets

KIT FOR LOCATING A VEIN

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science including medical preparations characterized by their physical form, more specifically, a composite device containing a pharmacologically active media. (A61K9/703)

SUMMARY OF INVENTION

The kit for locating a vein is a medical device. The kit for locating a vein is configured for use with a patient. The kit for locating a vein is configured for use in inserting an intravenous (IV) catheter into a targeted vein of the patient. The kit for locating a vein is a transparent structure. The kit for locating a vein removably attaches to the skin of the patient. The kit for locating a vein numbs the skin of the patient. The kit for locating a vein generates a vasomotor response that increases the flow of blood through the targeted vein thereby making the targeted vein larger and more visible. The transparent structure of the kit for locating a vein provides the ability to insert the IV catheter into the targeted vein while the kit for locating a vein remains attached to the patient. The kit for locating a vein forms a dressing that captures bodily fluids that are released during the insertion of the IV catheter.

The kit for locating a vein comprises a parchment sheeting, a working media, a transparent pocket, and a plurality of apertures. The parchment sheeting, the working media, and the transparent pocket form a transparent composite textile structure. The plurality of apertures are apertures that are formed through the composite textile structure that facilitate the insertion of the IV catheter into the targeted vein of the patient.

These together with additional objects, features and advantages of the kit for locating a vein will be readily apparent to those of ordinary skill in the art upon reading the following detailed description of the presently preferred, but nonetheless illustrative, embodiments when taken in conjunction with the accompanying drawings.

In this respect, before explaining the current embodiments of the kit for locating a vein in detail, it is to be understood that the kit for locating a vein is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the kit for locating a vein.

It is therefore important that the claims be regarded as including such equivalent construction insofar as they do not depart from the spirit and scope of the kit for locating a vein. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
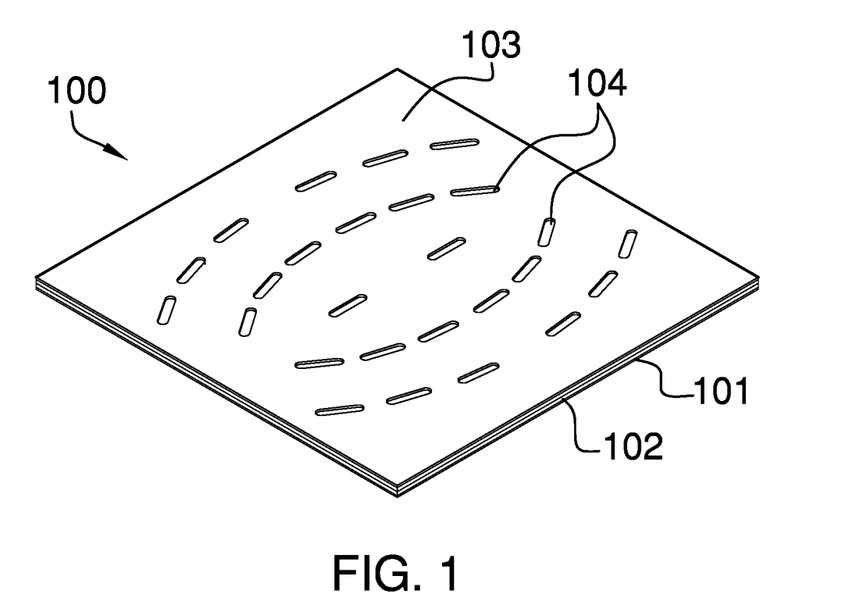
FIG. 1 is a perspective view of an embodiment of the disclosure.
Figure 2:
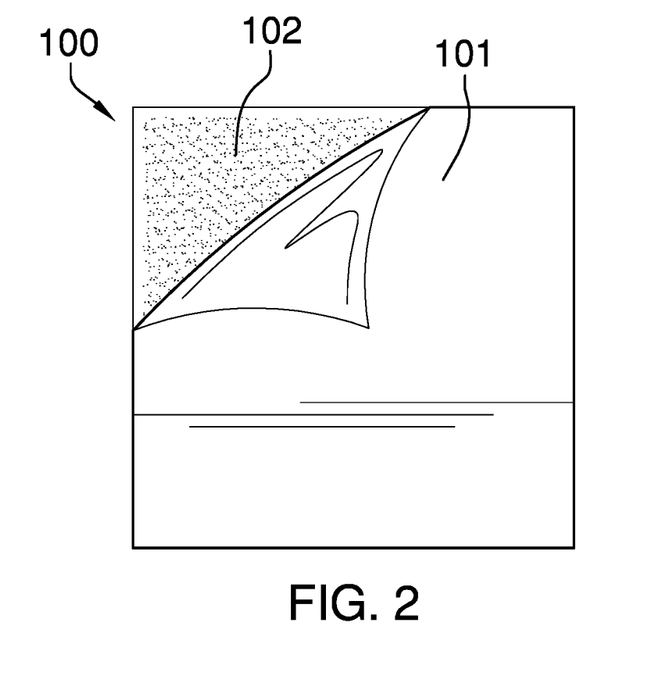
FIG. 2 is a rear view of an embodiment of the disclosure.
Figure 3:
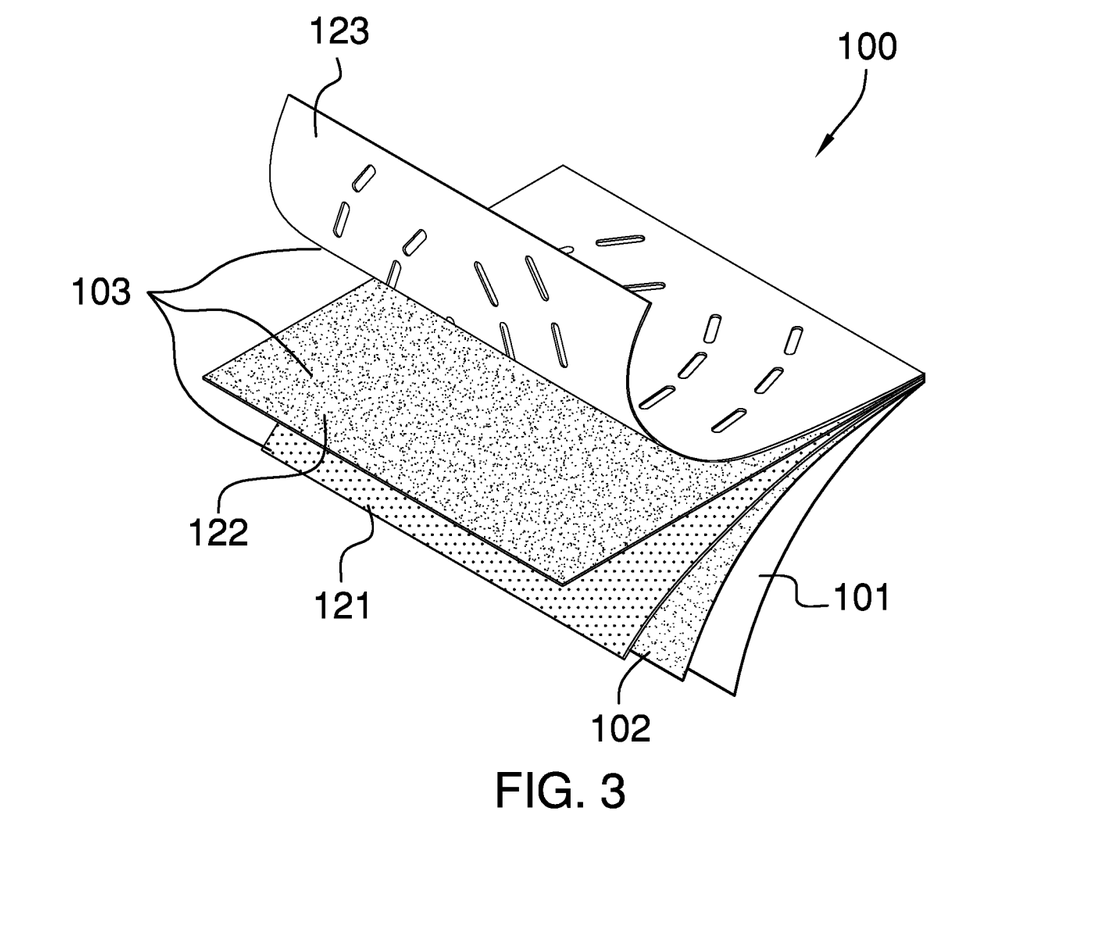
FIG. 3 is an exploded view of an embodiment of the disclosure.
Figure 4:
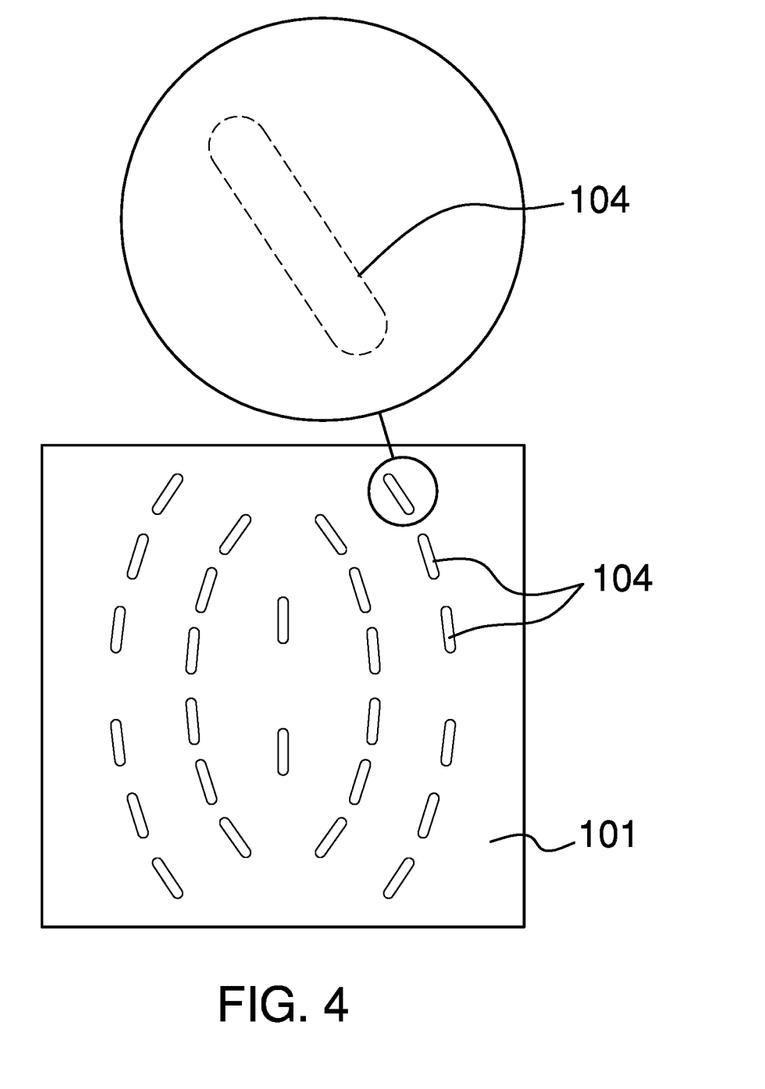
FIG. 4 is a front view of an embodiment of the disclosure.
Figure 5:
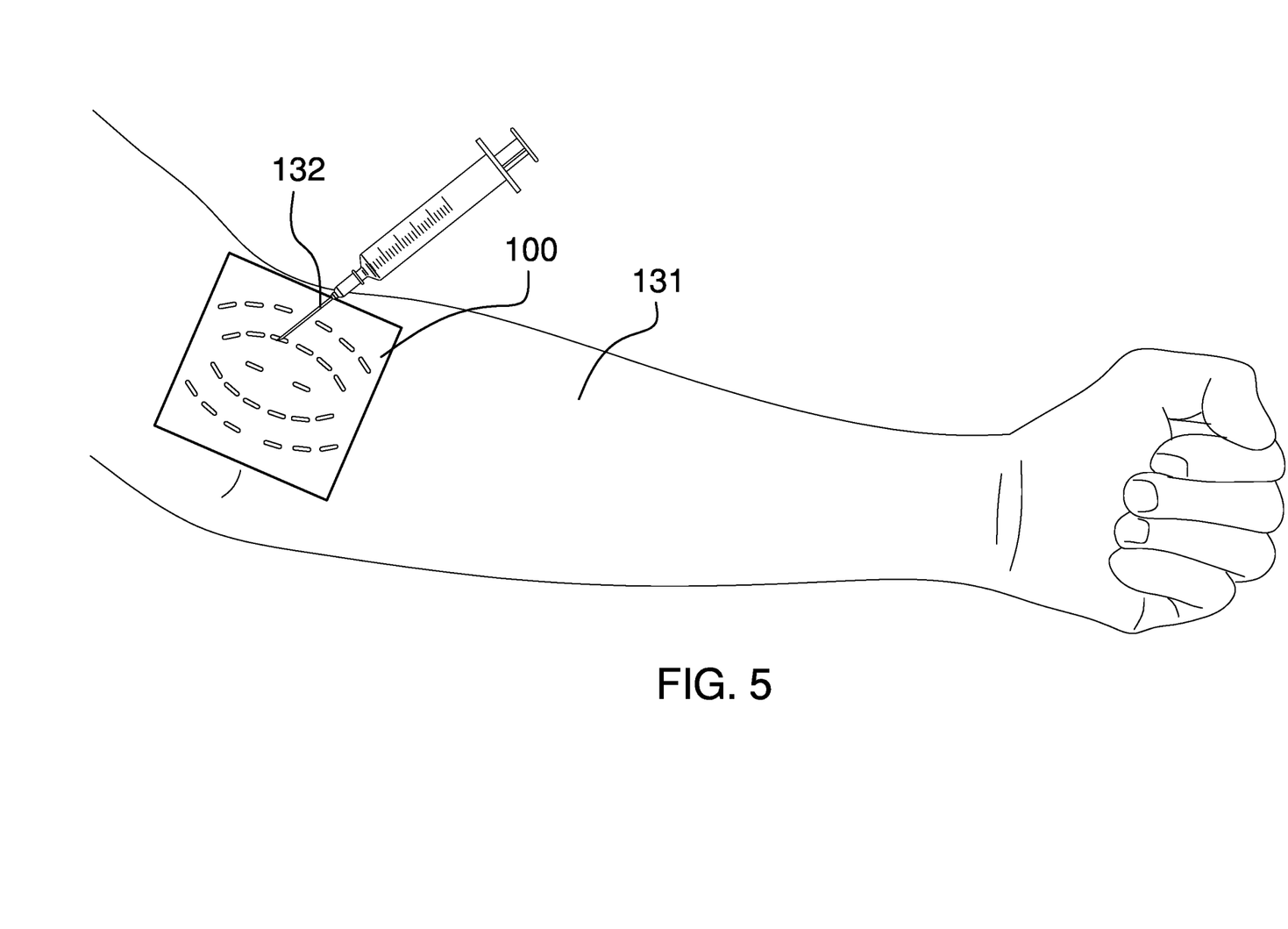
FIG. 5 is an in-use view of an embodiment of the disclosure.
Figure 6:
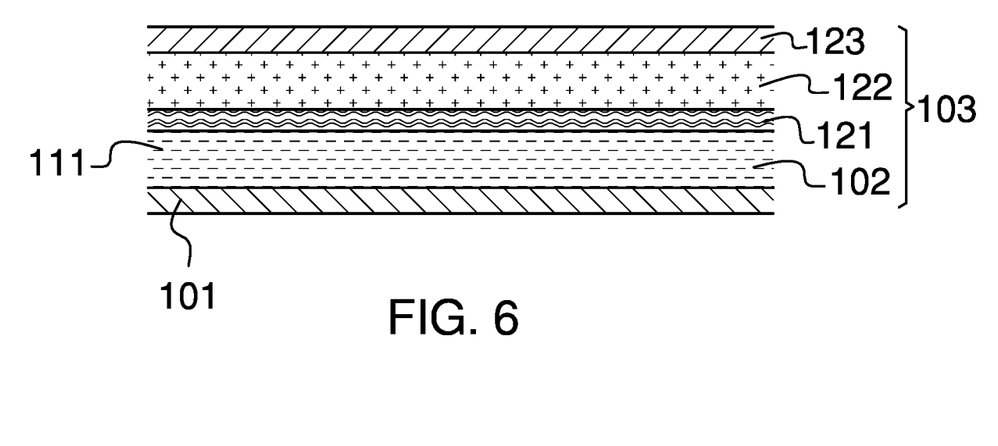
FIG. 6 is a detail view of an embodiment of the disclosure.
Figure 7:
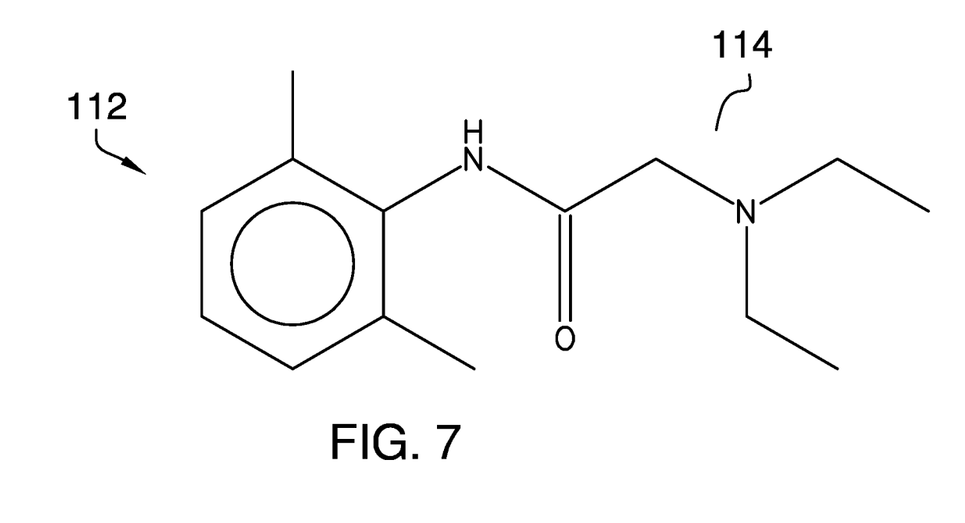
FIG. 7 is a detail view of an embodiment of the disclosure.
Figure 8:
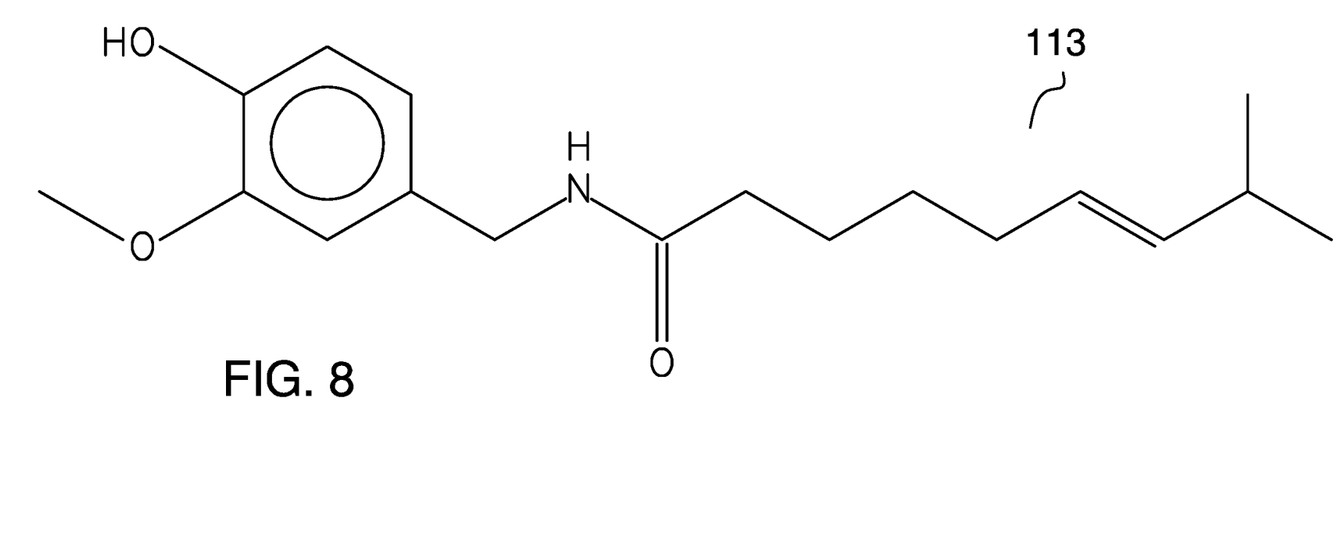
FIG. 8 is a detail view of an embodiment of the disclosure.

Detailed reference will now be made to one or more potential embodiments of the disclosure, which are illustrated in FIGS. 1 through 8.

The kit for locating a vein 100 (hereinafter invention) is a medical device. The invention 100 is configured for use with a patient 131. The invention 100 is configured for use in inserting an intravenous (IV) catheter into a targeted vein of the patient 131. The invention 100 is a transparent structure. The invention 100 removably attaches to the skin of the patient 131. The invention 100 numbs the skin of the patient 131. The invention 100 generates a vasomotor response that increases the flow of blood through the targeted vein of the patient 131 thereby making the targeted vein larger and more visible. The transparent structure of the invention 100 provides the ability to insert the IV catheter 132 into the targeted vein of the patient 131 while the invention 100 remains attached to the patient 131. The invention 100 forms a dressing that captures bodily fluids that are released during the insertion of the IV catheter 132.

The invention 100 comprises a parchment sheeting 101, a working media 102, a transparent pocket 103, and a plurality of apertures 104. The parchment sheeting 101, the working media 102, and the transparent pocket 103 forms a transparent composite textile structure. The plurality of apertures 104 are apertures that are formed through the composite textile structure that facilitate the insertion of the IV catheter 132 into the targeted vein of the patient 131. The patient 131 is defined elsewhere in this disclosure. The IV catheter 132 is defined elsewhere in this disclosure.

The parchment sheeting 101 is a sheeting. The parchment sheeting 101 encloses the working media 102 while the invention 100 is in storage. The parchment sheeting 101 forms a protected space that keeps the working media 102 clean until the invention 100 is required for use. In the first potential embodiment of the disclosure, the parchment sheeting 101 is formed from a silicone impregnated paper. The form factor of the parchment sheeting 101 is geometrically identical to the form factor of the transparent pocket 103. The parchment sheeting 101 attaches to the working media 102 such that the working media 102 is sandwiched between the parchment sheeting 101 and the transparent pocket 103 to form a disk-shaped composite textile structure The plurality of apertures 104 are apertures that are formed through the congruent ends of the disk-shaped composite textile structure of the invention 100. Each of the plurality of apertures 104 is sized such that the IV catheter 132 can be inserted through any aperture selected from the plurality of apertures 104 into the targeted vein of the patient 131. The plurality of apertures 104 are distributed across the congruent ends of the disk-shaped composite textile structure of the invention 100 such that the position of the IV catheter 132 can be adjusted to match variations in the location of the targeted vein of the patient 131. The plurality of apertures 104 forms a fluidic connection between the skin of the patient 131 and the transparent pocket 103 such that bodily fluids that are released during the insertion of the IV catheter 132 will flow into the transparent absorbent material contained in the transparent pocket 103 for collection.

The working media 102 is a chemical compound. The working media 102 is a transparent compound. The working media 102 is applied as a coating to the transparent pocket 103. Specifically, the working media 102 is applied as a coating to the exterior surface of the interior sheeting 121 of the transparent pocket 103. The working media 102 removably attaches the transparent pocket 103 to the skin of the patient 131. The working media 102 numbs the skin of the patient 131. The working media 102 heats the skin of the patient 131. The heating of the skin of the patient 131 generates a vasomotor response that increases the blood flow through the targeted vein of the patient 131. The working media 102 comprises an adhesive 111, an anesthetic 112, and an N-(4-oxy-3-methoxybenzyl)-8-methyl-6-nonenamide (CAS 404-86-4) 113.

The adhesive 111 is a chemical substance. The adhesive 111 is a removable adhesive 111. The adhesive 111 adheres the working media 102 and the transparent pocket 103 to the skin of the patient 131 such that the invention 100 can be removed from the skin of the patient 131 after use. The adhesive 111 is defined elsewhere in this disclosure.

The anesthetic 112 is a chemical substance. The anesthetic 112 is applied to the skin of the patient 131 when the working media 102 is placed against the skin of the patient 131. The anesthetic 112 is a pharmacologically active media that numbs the skin of the patient 131 during the use of the invention 100. The anesthetic 112 reduces the pain caused by the insertion of the IV catheter 132 into the targeted vein of the patient 131.

In the first potential embodiment of the disclosure, the anesthetic 112 is 2-(diethylamino)-N-(2,6-dimethylphenyl) acetamide (CAS 137-58-6) 114. The 2-(diethylamino)-N-(2,6-dimethylphenyl)acetamide (CAS 137-58-6) 114 is a topical anesthetic commonly used for relieving pain on the surface of the skin of the patient 131.

The N-(4-oxy-3-methoxybenzyl)-8-methyl-6-nonenamide (CAS 404-86-4) 113 is a chemical substance. The N-(4-oxy-3-methoxybenzyl)-8-methyl-6-nonenamide (CAS 404-86-4) 113 is applied to the skin of the patient 131 when the working media 102 is placed against the skin of the patient 131. The N-(4-oxy-3-methoxybenzyl)-8-methyl-6-nonenamide (CAS 404-86-4) 113 is a pharmacologically active media that heats the skin of the patient 131 during the use of the invention 100. The warmth generated by the N-(4-oxy-3-methoxybenzyl)-8-methyl-6-nonenamide (CAS 404-86-4) 113 generates a vasomotor response that dilates the targeted vein of the patient 131. The dilation of the targeted vein of the patient 131 makes it easier to insert the IV catheter 132 into the targeted vein of the patient 131.

The adhesive 111, the anesthetic 112, and the N-(4-oxy-3-methoxybenzyl)-8-methyl-6-nonenamide (CAS 404-86-4) 113 are mixed into a homogenous compound that forms the working media 102 that is applied as a coating to the exterior surface of the interior sheeting 121 of the transparent pocket 103.

The adhesive 111, the anesthetic 112, the N-(4-oxy-3-methoxybenzyl)-8-methyl-6-nonenamide (CAS 404-86-4) 113, and the 2-(diethylamino)-N-(2,6-dimethylphenyl)acetamide (CAS 137-58-6) 114 are defined elsewhere in this disclosure.

The transparent pocket 103 is a containment structure. The transparent pocket 103 is a transparent structure. The transparent pocket 103 contains a transparent absorbent material that forms a dressing that captures bodily fluids that are released during the insertion of the IV catheter 132. The transparent pocket 103 comprises an interior sheeting 121, a transparent absorbent acrylic dressing 122, and an exterior sheeting 123.

The interior sheeting 121 is a fluid impermeable sheeting. The interior sheeting 121 is a transparent plastic sheeting. The interior sheeting 121 forms an interior layer of the composite textile structure of the invention 100. The interior sheeting 121 forms a barrier between the transparent absorbent acrylic dressing 122 and the working media 102. The exterior surface of the interior sheeting 121 is the surface of the interior sheeting 121 that is distal from the transparent absorbent acrylic dressing 122. The working media 102 is applied as a coating to the exterior surface of the interior sheeting 121.

The transparent absorbent acrylic dressing 122 is an absorbent material. The transparent absorbent acrylic dressing 122 is sandwiched between the interior sheeting 121 and the exterior sheeting 123. The transparent absorbent acrylic dressing 122 forms a bandage that captures bodily fluids that are released during the insertion of the IV catheter 132 into the targeted vein of the patient 131. The bodily fluids that are released during the insertion of the IV catheter 132 flow into the transparent absorbent acrylic dressing 122 through the plurality of apertures 104. The transparent absorbent acrylic dressing 122 is formed as a transparent structure. The transparent absorbent acrylic dressing 122 is commercially available.

The exterior sheeting 123 is a fluid impermeable sheeting. The exterior sheeting 123 is a transparent plastic sheeting. The exterior sheeting 123 forms an exterior surface of the composite textile structure of the invention 100. The exterior sheeting 123 is the layer of the composite textile structure of the invention 100 that is distal from the skin of the patient 131. The exterior sheeting 123 forms a protected space around the transparent absorbent acrylic dressing 122. The form factor of the exterior sheeting 123 is geometrically identical to the form factor of the interior sheeting 121. The perimeters of the exterior sheeting 123 and the interior sheeting 121 are joined with a seam such that the transparent absorbent acrylic dressing 122 is contained within an enclosed space formed by the exterior sheeting 123 and the interior sheeting 121.

The transparent structures of the working media 102, the interior sheeting 121, the transparent absorbent acrylic dressing 122, and the exterior sheeting 123 combine to form a transparent composite textile structure. The transparent structure of the composite textile structure that forms the invention 100 allows for the skin of the patient 131 to be seen during the procedure to insert the IV catheter 132 into the targeted vein of the patient 131.

The following definitions were used in this disclosure:

Absorbent: As used in this disclosure, absorbent is an adjective that refers to a material that is able to soak up a liquid such as water.

Acrylic: As used in this disclosure, acrylic refers to a polymer or copolymer structure that comprises acrylic acid.

Acrylic Acid. As used in this disclosure, acrylic acid is a chemical compound with the chemical formula $C_3H_4O_2$. Acrylic acid is also known as 2-propenoic acid (CAS 79-10-7).

Adhesive: As used in this disclosure, an adhesive is a chemical substance that can be used to adhere two or more objects to each other. Types of adhesives include, but are not limited to, epoxies, polyurethanes, polyimides, or cyanoacrylates, silicone, or latex based adhesives.

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Anesthetic: As used in this disclosure, an anesthetic is a pharmacologically active media that reduces or eliminates the sensitivity of a patient to pain. A topical anesthetic is applied to the skin of the patient to provide local pain relief. Lidocaine (2-(diethylamino)-N-(2,6-dimethylphenyl)acetamide (CAS 137-58-6)) is a commonly used topical anesthetic.

Aperture: As used in this disclosure, an aperture is a prism-shaped negative space that is formed completely through a structure or the surface of a hollow structure.

Bandage: As used in this disclosure, a bandage is an absorbent that is used to cover, dress, protect, or treat a wound. A bandage that is formed from a mesh is commonly referred to as a gauze. The term dressing is a synonym for a bandage.

Catheter: As used in this disclosure, a catheter is a flexible tube that is inserted into the body through which images may be captured and fluids may be introduced into or removed from the body. Endoscope is a synonym for catheter.

Coating: As used in this disclosure, a coating refers to a substance that is applied to the surface of an object such that the coating forms a new surface of the object. A coating is commonly said to be formed as a layer. Paint is an example of a common coating material.

Composite Prism: As used in this disclosure, a composite prism refers to a structure that is formed from a plurality of structures selected from the group consisting of a prism structure and a pyramid structure. The plurality of selected structures may or may not be truncated. The plurality of prism structures are joined together such that the center axes of each of the plurality of structures are aligned. The congruent ends of any two structures selected from the group consisting of a prism structure and a pyramid structure need not be geometrically similar.

Composite Textile: As used in this disclosure, a composite textile is a multilayer fabric made of two or more joined layers of textile or sheeting materials.

Copolymer: As used in this disclosure, a copolymer is a polymer formed from two or more repeating molecules (also referred to as monomers).

Correspond: As used in this disclosure, the term correspond is used as a comparison between two or more objects wherein one or more properties shared by the two or more objects match, agree, or align within acceptable manufacturing tolerances.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Exterior: As used in this disclosure, the exterior is used as a relational term that implies that an object is not contained within the boundary of a structure or a space.

Fluid: As used in this disclosure, a fluid refers to a state of matter wherein the matter is capable of flow and takes the shape of a container it is placed within. The term fluid commonly refers to a liquid or a gas.

Form Factor: As used in this disclosure, the term form factor refers to the size and shape of an object.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1.

Interior: As used in this disclosure, the interior is used as a relational term that implies that an object is contained within the boundary of a structure or a space.

Liquid: As used in this disclosure, a liquid refers to a state (phase) of matter that is fluid and that maintains, for a given pressure, a fixed volume that is independent of the volume of the container.

Monomer: As used in this disclosure, a monomer refers to a molecular structure that bonds to itself in a repeating manner to form a polymer.

N-(4-oxy-3-methoxybenzyl)-8-methyl-6-nonenamide: As used in this disclosure, N-(4-oxy-3-methoxybenzyl)-8-methyl-6-nonenamide (CAS 404-86-4) is a pharmacologically active media derived from the pepper plant. N-(4-oxy- 3-methoxybenzyl)-8-methyl-6-nonenamide (CAS 404-86-4) is commonly known as capsaicin. N-(4-oxy-3-methoxybenzyl)-8-methyl-6-nonenamide (CAS 404-86-4) is applied topically for pain relief. N-(4-oxy-3-methoxybenzyl)-8-methyl-6-nonenamide (CAS 404-86-4) also has benefits in metabolic regulation and the treatment of prostate cancer.

One to One: When used in this disclosure, a one to one relationship means that a first element selected from a first set is in some manner connected to only one element of a second set. A one to one correspondence means that the one to one relationship exists both from the first set to the second set and from the second set to the first set. A one to one fashion means that the one to one relationship exists in only one direction.

Perimeter: As used in this disclosure, a perimeter is one or more curved or straight lines that bounds an enclosed area on a plane or surface. The perimeter of a circle is commonly referred to as a circumference.

Organic: As used in this disclosure, organic refers to a carbon-based chemical structure. A limited number of carbon-based salts are traditionally considered inorganic chemical structures and are excluded from the study of organic chemistry.

Parchment: As used in this disclosure, parchment refers to a silicone impregnated sheet of paper. Parchment is known for having high-temperature resistance and for resisting saturation by a liquid.

Perimeter: As used in this disclosure, a perimeter is one or more curved or straight lines that bounds an enclosed area on a plane or surface. The perimeter of a circle is commonly referred to as a circumference.

Pharmacologically Active Media: As used in this disclosure, a pharmacologically active media refers to a chemical substance that has a biochemical or physiological effect on a biological organism.

Plastic: As used in this disclosure, plastic refers to a manufactured material that is formed from a structure selected from the group consisting of a polymer or a copolymer. Unless stated otherwise, this disclosure assumes that the plastic is formed from organic monomers.

Polymer: As used in this disclosure, a polymer refers to a molecular chain that comprises multiple repeating units known as monomers. The repeating unit may be an atom or a molecular structure.

Pressure Sensitive Adhesive: As used in this disclosure, a pressure sensitive adhesive is an adhesive that is a permanently tacky adhesive that is activated by the application of pressure.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Protected Space: As used in this disclosure, a protected space is a space formed by a boundary structure. The boundary structure forms a barrier that protects objects within the protected space from potential dangers from the other side of the boundary.

Removable Adhesive: As used in this disclosure, a removable adhesive is a commercially available adhesive that is designed with a lower tack, or stickiness, such that a first object is attached to a second object with a removable adhesive the first object can be readily removed in a manner that ideally, though not necessarily practically, leaves behind no adhesive residue on the second object. A repositionable adhesive is a subset of removable adhesives that are intended to allow the first object to be reattached to a third object or the second object in the initial or a different position. Within this disclosure, a removable adhesive is assumed to include repositionable adhesives.

Sandwich: As used in this disclosure, to sandwich means to insert a first disk-shaped structure between a second disk-shaped structure and a third disk-shaped structure to form a composite prism structure. Specifically: a) a first congruent end of the first disk-shaped structure is placed against a first interior congruent end of the second disk-shaped structure; and, b) a second congruent end of the first disk-shaped structure is placed against a second interior congruent end of the third disk-shaped structure. A first exterior congruent end of the second disk-shaped structure forms a first overall congruent end of the overall composite prism structure described in this definition. A second exterior congruent end of the third disk-shaped structure forms a second overall congruent end of the overall composite prism structure described in this definition. The second overall congruent end of the overall composite prism structure is distal from the first overall congruent end.

Seam: As used in this disclosure, a seam is a joining of: 1) a first textile to a second textile; 2) a first sheeting to a second sheeting; or, 3) a first textile to a first sheeting. Potential methods to form seams include, but are not limited to, a sewn seam, a heat bonded seam, an ultrasonically bonded seam, a laser seam, or a seam formed using an adhesive.

Sheeting: As used in this disclosure, a sheeting is a material, such as a paper, textile, a plastic, or a metal foil, in the form of a thin flexible layer or layers. The sheeting forms a disk structure. The two surfaces of the sheeting with the greatest surface area are called the faces of the sheeting.

Silicone: As used in this disclosure, silicone is a substance formed from silicon (Si) and oxygen (O) that forms the backbone of polymer type chains similar to polymers that are formed by carbon. Though exceptions do exist, silicone is generally considered to be less reactive and to have better heat resistance when compared to most common carbon-based polymers.

Textile: As used in this disclosure, a textile is a material that is woven, knitted, braided or felted. Synonyms in common usage for this definition include fabric and cloth. The two surfaces of the textile with the greatest surface area are called the faces of the textile.

Transparent: As used in this disclosure, transparent refers to a material that allows light to pass through the material without significant scattering such that an object can be clearly seen through the material.

With respect to the above description, it is to be realized that the optimum dimensional relationship for the various components of the invention described above and in FIGS. 1 through 8 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A medical device comprising
a parchment sheeting, a working media, a transparent pocket, and a plurality of apertures;
wherein the parchment sheeting, the working media, and the transparent pocket forms a transparent composite textile structure;
wherein the plurality of apertures are apertures that are formed through the composite textile structure;
wherein the medical device is configured for use with a patient;
wherein the medical device is configured for use in inserting an intravenous (IV) catheter into a targeted vein of the patient;
wherein the working media comprises an adhesive, an anesthetic, and an N-(4-oxy-3-methoxybenzyl)-8-methyl-6-nonenamide (CAS 404-86-4);
wherein the plurality of apertures are apertures that are formed through the congruent ends of the disk-shaped composite textile structure of the medical device;
wherein each of the plurality of apertures is sized such that the IV catheter inserts through any aperture selected from the plurality of apertures into the targeted vein of the patient;
wherein the plurality of apertures forms a fluidic connection between the skin of the patient and the transparent pocket such that bodily fluids that are released during the insertion of the IV catheter will flow into the transparent absorbent material contained in the transparent pocket for collection;
wherein the transparent pocket comprises an interior sheeting, a transparent absorbent acrylic dressing, and an exterior sheeting;
wherein the transparent absorbent acrylic dressing is sandwiched between the interior sheeting and the exterior sheeting.

2. The medical device according to claim 1
wherein the medical device is a transparent structure;
wherein the medical device removably attaches to the skin of the patient;
wherein the medical device numbs the skin of the patient;
wherein the medical device generates a vasomotor response that increases the flow of blood through the targeted vein of the patient thereby making the targeted vein larger and more visible;
wherein the transparent structure of the medical device allows for the insertion of the IV catheter into the targeted vein of the patient while the medical device remains attached to the patient;
wherein the medical device forms a dressing that captures bodily fluids that are released during the insertion of the IV catheter.

3. The medical device according to claim 2
wherein the parchment sheeting is a sheeting;
wherein the parchment sheeting encloses the working media;
wherein the parchment sheeting forms a protected space.

4. The medical device according to claim 3
wherein the form factor of the parchment sheeting is geometrically identical to the form factor of the transparent pocket;
wherein the parchment sheeting attaches to the working media such that the working media is sandwiched between the parchment sheeting and the transparent pocket to form a disk-shaped composite textile structure.

5. The medical device according to claim 4
wherein the working media is a chemical compound;
wherein the working media is a transparent compound;
wherein the working media is applied as a coating to the transparent pocket.

6. The medical device according to claim 5
wherein the working media removably attaches the transparent pocket to the skin of the patient;
wherein the working media numbs the skin of the patient;
wherein the working media heats the skin of the patient.

7. The medical device according to claim 6
wherein the transparent pocket is a containment structure;
wherein the transparent pocket is a transparent structure;
wherein the transparent pocket contains a transparent absorbent material that forms a dressing that captures bodily fluids that are released during the insertion of the IV catheter.

8. The medical device according to claim 7
wherein the adhesive, the anesthetic, and the N-(4-oxy-3-methoxybenzyl)-8-methyl-6-nonenamide (CAS 404-86-4) are mixed into a homogenous compound that forms the working media.

9. The medical device according to claim 8
wherein the adhesive is a chemical substance;
wherein the adhesive is a removable adhesive;
wherein the adhesive adheres the working media and the transparent pocket to the skin of the patient such that the medical device can be removed from the skin of the patient after use.

10. The medical device according to claim 9
wherein the anesthetic is a chemical substance;
wherein the anesthetic is applied to the skin of the patient when the working media is placed against the skin of the patient;
wherein the anesthetic is a pharmacologically active media that numbs the skin of the patient during the use of the medical device;
wherein the anesthetic reduces the pain caused by the insertion of the IV catheter into the targeted vein of the patient.

11. The medical device according to claim 10
wherein the N-(4-oxy-3-methoxybenzyl)-8-methyl-6-nonenamide (CAS 404-86-4) is a chemical substance;
wherein the N-(4-oxy-3-methoxybenzyl)-8-methyl-6-nonenamide (CAS 404-86-4) is applied to the skin of the patient when the working media is placed against the skin of the patient;
wherein the N-(4-oxy-3-methoxybenzyl)-8-methyl-6-nonenamide (CAS 404-86-4) is a pharmacologically active media that heats the skin of the patient.

12. The medical device according to claim 11
- wherein the interior sheeting is a fluid impermeable sheeting;
- wherein the interior sheeting is a transparent plastic sheeting;
- wherein the interior sheeting forms an interior layer of the composite textile structure of the medical device.

13. The medical device according to claim 12
- wherein the interior sheeting forms a barrier between the transparent absorbent acrylic dressing and the working media;
- wherein the exterior surface of the interior sheeting is the surface of the interior sheeting that is distal from the transparent absorbent acrylic dressing;
- wherein the working media is applied as a coating to the exterior surface of the interior sheeting.

14. The medical device according to claim 12
- wherein the transparent absorbent acrylic dressing is an absorbent material;
- wherein the transparent absorbent acrylic dressing is formed as a transparent structure;
- wherein the transparent absorbent acrylic dressing forms a bandage that captures bodily fluids that are released during the insertion of the IV catheter into the targeted vein of the patient.

15. The medical device according to claim 14 wherein the bodily fluids that are released during the insertion of the IV catheter flow into the transparent absorbent acrylic dressing through the plurality of apertures.

16. The medical device according to claim 15
- wherein the exterior sheeting is a fluid impermeable sheeting;
- wherein the exterior sheeting is a transparent plastic sheeting;
- wherein the exterior sheeting forms an exterior surface of the composite textile structure of the medical device;
- wherein the exterior sheeting is the layer of the composite textile structure of the medical device that is distal from the skin of the patient;
- wherein the exterior sheeting forms a protected space around the transparent absorbent acrylic dressing;
- wherein the form factor of the exterior sheeting is geometrically identical to the form factor of the interior sheeting.

17. The medical device according to claim 16 wherein the perimeters of the exterior sheeting and the interior sheeting are joined with a seam such that the transparent absorbent acrylic dressing is contained within an enclosed space formed by the exterior sheeting and the interior sheeting.

18. The medical device according to claim 17
- wherein the parchment sheeting is formed from a silicone impregnated paper;
- wherein the anesthetic is 2-(diethylamino)-N-(2,6-dimethylphenyl)acetamide (CAS 137-58-6).

* * * * *